United States Patent [19]

Sieverding

[11] Patent Number: 4,699,146
[45] Date of Patent: Oct. 13, 1987

[54] HYDROPHILIC, ELASTOMERIC, PRESSURE-SENSITIVE ADHESIVE

[75] Inventor: David L. Sieverding, Boulder, Colo.

[73] Assignee: Valleylab, Inc., Boulder, Colo.

[21] Appl. No.: 775,187

[22] Filed: Sep. 12, 1985

Related U.S. Application Data

[63] Continuation of Ser. No. 528,679, Sep. 1, 1983, abandoned, which is a continuation-in-part of Ser. No. 352,268, Feb. 25, 1982, abandoned.

[51] Int. Cl.$^4$ .................. C08F 2/54; C08K 13/02; C08K 5/05; C08L 39/06
[52] U.S. Cl. .................... 128/640; 128/798; 252/518; 252/521; 522/79; 522/86; 522/152
[58] Field of Search .................... 522/86, 152, 79; 128/639, 640, 641, 798, 802–803, 303.13; 252/518, 521

[56] References Cited

U.S. PATENT DOCUMENTS

| | | | |
|---|---|---|---|
| 3,357,930 | 12/1967 | Marks | 252/518 |
| 4,089,832 | 5/1978 | Yamauchi | 524/516 |
| 4,094,822 | 6/1978 | Kater | 252/518 |
| 4,554,924 | 11/1985 | Engel | 252/500 |

FOREIGN PATENT DOCUMENTS 1138 6/1980 PCT Int'l Appl. .

Primary Examiner—John C. Bleutge
Assistant Examiner—A. H. Koeckert
Attorney, Agent, or Firm—Peter C. Richardson; Lawrence C. Akers; Gezina Holtrust

[57] ABSTRACT

The present invention concerns a novel water-insoluble, hydrophilic, pressure-sensitive adhesive that has a number of unique characteristics including being elastomeric and ultraconformable. This adhesive includes an irradiation cross-linked synthetic organic polymer having a three-dimensional matrix, and an adhesive plasticizer. The plasticizer includes a substantially non-volatile elasticizer. The adhesive is useful either as a coating on a supporting web-like substrate or as a self-supporting layer. Also provided are various articles made using the adhesive such as a bandage or ostomy device, a method of making the adhesive, and methods of using the adhesive.

In one embodiment, the adhesive is electroconductive, and is useful for attaching an electrically conductive member of an electrode to a selected surface such as mammalian tissue. Also provided is an electrode having a layer of this adhesive, and a method of adhering this electrode to mammalian tissue.

13 Claims, 3 Drawing Figures

HYDROPHILIC, ELASTOMERIC, PRESSURE-SENSITIVE ADHESIVE

This is a continuation of application Ser. No. 528,679, filed on Sept. 1, 1983, now abandoned, which is a continuation-in-part of application Ser. No. 352,268, filed Feb. 25, 1982, now abandoned.

TECHNICAL FIELD

This invention relates to a novel pressure-sensitive adhesive, and particularly relates to a water-insoluble, hydrophilic, elastomeric, pressure-sensitive adhesive. This invention additionally relates to a supportive web-like substrate such as that of an ostomy appliance, coated with this adhesive, to a self-supporting layer of the adhesive, to various articles made of this self-supporting layer, to methods of using the self-supporting layer, to a method of making the adhesive, to a type of the adhesive that is electroconductive, and to an electrode such as an electrosurgical return electrode comprising this type of the adhesive.

BACKGROUND ART

A polymeric hydrophobic substance is the most common type of conventional pressure-sensitive adhesive used to secure substrates to the human body. The majority of all adhesive bandages are made with this broad class of adhesive, which is used as a thin film. These polymeric hydrophobic substances are frequently produced by homopolymerization or copolymerization of one or more vinyl type monomers, especially acrylic esters, methacrylic esters, vinyl alcohol esters and vinyl ethers. Natural rubber and gum have also found use in conventional adhesive formulae.

When these prior art thin film, hydrophobic, polymeric, pressure-sensitive adhesives are used to secure a device such as an EKG monitoring electrode or to secure a bandage, removal frequently causes trauma, discomfort and soreness to the skin to which the adhesive was adhered. Skin trauma of this type may take the form of pulled hair, bruises, erythema, edema, blistering, removal of some epidermis, or tearing of the skin. The severity of the discomfort and trauma appears to be greater when the adhesive is allowed to contact the skin for an extended time. Frequently, EKG monitoring electrodes and postsurgical bandages are left on a patient's skin for up to a week and sometimes longer. Thus, the removal of these bandages and electrodes, quite often, is very painful, and soreness persists for some time.

Hydrophilic polymeric pressure-sensitive adhesives are also known in the prior art. Adhesives of this type are much less common than hydrophoboic pressure-sensitive adhesives. Major uses of hydrophilic pressure-sensitive adhesives include use as an ostomy adhesive and as a conductive adhesive for securing an electrode to the human body. These pressure-sensitive adhesives are much less likely to cause skin trauma than the hydrophobic-type adhesives.

Some hydrophilic-type adhesives are made by chemically cross-linking a polymeric material to form the adhesive. Illustrative of this type of prior art are U.S. Pat. No. 3,998,215 to Anderson et al, U.S. Pat. No. 4,125,110 to Hymes, British Patent Application No. 2,034,184 of Hymes, U.S. Pat. No. 4,066,078 to Berg, and U.S. Pat. No. 4,094,822 to Kater. The adhesive of each of these documents is used in a patient electrode, and is conductive per se or provided with conductivity by, for example, using the adhesive to bond strands of a conductive material. In the Anderson et al, Hymes and Kater documents, it is stated that the adhesive is formed from an aqueous solution of the polymeric material.

In the Anderson et al patent, a porous webbed material is dipped into an aqueous solution of a hydrogel former, for example, polyvinyl alcohol, to wet the webbed material, excess solution is scraped off, and the webbed material is then dipped into a solution of a gel-forming agent or a cross-linker for the hydrogel former, in order to form a hydrogel throughout the webbed material. The hydrogel is said to be lightly adherent to the body surface but sufficiently cohesive so that no residue remains upon removal thereof.

The Hymes patent relates to an electrode having an electrically conductive adhesive that contains a hydrophilic polysaccharide material (karaya), a hydric alcohol (glycerin) to provide plasticity, an electrolytic salt and propylene glycol. An alternate embodiment of this adhesive includes additive materials for cross-linking the hydrophilic polysaccharide material. These chemical cross-linking agents are said to include, for example, gelatin, polyvinyl acetate, certain polyesters and calcium salts.

The British patent application in the name of Hymes is similar to the U.S. patent to Hymes. The adhesive of this document is formed from dry karaya gum powder and a non-volatile liquid carrying either an ionizable salt or finely powdered silver or aluminum. In an alternate embodiment, the adhesive is comprised of 15-70% aqueous polyacrylic acid (25% concentration), 15-45% karaya, 10-35% water, 0-35% isopropyl alcohol, and 1-3% electrolyte. Additive materials for chemically cross-linking the karaya are said to include polymers such as vinyl acetate-ethylene copolymers and polyacrylic acid. At page 7, lines 48-50, it is mentioned that the substrate compound can be subjected to radiation to inhibit microbial growth, and that such radiation should be below 2.5 megarads gamma radiation.

The Kater patent pertains to an electrode having an adhesive-electrolyte material. Polyvinyl alcohol adhesives are said to be preferred, and a formulation is provided for an adhesive of this type, in which there is present 15-25% polyvinyl alcohol having a degree of polymerization equal to 1700 and being 88% hydrolyzed, and 5-10% glycerol. Suitably, the adhesive-electrolyte material is based upon polyvinylpyrrolidone (PVP), polyacrylamide or polyvinylpyridines.

The Berg patent, mentioned above, is concerned with an electrode having an electrically conductive, hydrophilic adhesive that is a chemically cross-linked hydrophilic interpolymer composition. The starting materials for preparing this interpolymer composition may be (a) an ester of an $\alpha,\beta$-olefinically unsaturated carboxylic acid and a monohydric or polyhydric alcohol having a terminal quaternary ammonium group, and (b) an $\alpha,\beta$-olefinically unsaturated comonomer.

Other documents relating to an adhesive for use in a patient electrode include British Patent Application No. 2,045,088 in the name of Larimore, U.S. Pat. No. 4,237,886 to Sakurada et al, U.S. Pat. No. 4,243,051 to Wittemann, U.S. Pat. No. 4,243,052 to Bailey, U.S. Pat. No. 4,248,247 to Ware et al, U.S. Pat. No. 4,267,840 to Lazar et al, U.S. Pat. No. 3,547,105 to Paine, U.S. Pat. No. 3,565,059 to Hauser et al, U.S. Pat. No. 3,607,788 to Adolph et al, U.S. Pat. No. 3,911,906 to Reinhold, Jr., U.S. Pat. No. 3,993,049 to Kater, U.S. Pat. No.

4,008,721 to Burton, U.S. Pat. No. 4,016,869 to Reichenberger, U.S. Pat. No. 4,067,342 to Burton, U.S. Pat. No. 4,112,941 to Larimore, U.S. Pat. No. 4,141,366 to Cross, Jr. et al, U.S. Pat. No. Re. 24,906 to Ulrich, U.S. Pat. No. 3,845,757 to Weyer and U.S. Pat. No. 3,265,638 to Goodman et al. The Larimore British Patent application and the Sakurada et al, Wittemann, Bailey, Ware et al and Lazar et al patents appear to be concerned with adhesives based upon cross-linked polymers. The patents to Reinhold, Jr., Larimore, Burton and Cross, Jr. et al pertain to an adhesive material based upon an acrylic polymer. Of these patents, the patent to Reinhold, Jr., has electrically conductive particles dispersed throughout the adhesive material thereof. An adhesive layer of this type can create non-uniform electrical transmission, provide lower conductivity, require a high cost for manufacture, be difficult to manufacture, have lower adhesivity, and be unable to absorb perspiration, with there being a tendency to lose adhesion if only a slight amount of moisture is present. The Kater patent discloses that the adhesive thereof is suitably PVP-based. The Goodman et al patent is concerned with an electrolyte composition comprising an aqueous solution of sodium chloride that is preferably completely saturated with silver chloride and that contains up to 7.5% polyvinyl alcohol as a thickening agent. It is said that borax may be used to aid the polyvinyl alcohol in its thickening action.

Other patents pertaining to chemically cross-linking an aqueous solution of a polymeric material include U.S. Pat. No. 3,087,920 to Suzumura et al, U.S. Pat. No. 4,036,808 to Rembaum et al, U.S. Pat. No. 3,932,311 to Caldwell et al, U.S. Pat. No. 2,616,818 to Azorlosa, U.S. Pat. No. 4,089,832 to Yamauchi et al, U.S. Pat. No. 3,220,960 to Wichterle, U.S. Pat. No. 3,545,230 to Morse, U.S. Pat. No. 3,336,129 to Herrett et al, and U.S. Pat. No. 2,838,421 to Sohl. The Suzumura et al patent is concerned with a cold water-soluble polyvinyl alcohol that includes an admixture of partially saponified polyvinyl alcohol having a hydrolysis of 75-90%, a diaminostilbene optical bleaching agent, and a surfactant. At column 3, lines 33-35, of this patent, it is stated that in water, the partially saponified polyvinyl alcohol reacts with the diaminostilbene to form a three-dimensional bridge, thereby assuming a gel form, and at column 3, line 47, the cold water-soluble polyvinyl alcohol is stated to be useful as an adhesive.

The Rembaum et al patent relates to a conductive hydrogel formed by reacting the cationic polyelectrolyte thereof with a gel-forming polymer such as polyvinyl alcohol, polyacrylic acid or a polyether. At column 8, lines 19-22, it is explained that a cross-linked hydrogel can be prepared from aqueous solutions of a mixture of polyvinyl alcohol and polyacrylic acid or polyhydroxyethylmethacrylate. The gels of this patent appear to be adhesive.

The Caldwell et al patent is concerned with an electrically conducting adhesive composition containing a cross-linked acrylate and/or methacrylate polymer and silver particles. The Azorlosa patent relates to a process for preparing a coated paper in which polyacrylamide or a copolymer of acrylamide and acrylic acid is used as an adhesive. In a preferred embodiment, the coated paper is treated with a cross-linking agent so as to render the adhesive highly insoluble and strongly adhesive.

The Yamauchi et al patent pertains to a water-containing plastic composition that contains a water-containing powdery gel obtained by subjecting a water-soluble polymer such as polyvinyl alcohol, polyacrylamide or PVP to a cross-linking reaction and then pulverizing the cross-linked product. Ionizing radiation can be used to effect the cross-linking. The plastic composition is suitable for manufacturing poorly combustible molding materials.

The Wichterle patent is concerned with a hydrogel essentially consisting of a cross-linked hydrophilic polymer and 20-97% of an aqueous liquid. The hydrogel can be made, cut, or otherwise shaped to produce, for example, a lens, a pessary, or a dialyzer diaphragm. Medicinally active agents such as antibiotics may be dissolved in the aqueous constituent to provide medication over an extended period.

The Morse patent relates to a flexible cooling device comprised of a reinforced layer of an insoluble hydrophilic gel. If desired, the gel can include materials to control the physical and chemical properties such as freezing point and chemical stability. Exemplary starting materials for preparing the gel include poly(ethylene oxide), PVP, polyacrylamide, polyvinyl alcohol, maleic anhydride-vinyl ether copolymers, polyacrylic acid, ethylene-maleic anhydride copolymers, polyvinyl ether, polyethyleneimine, polyvinyl alkyl pyridinium halides, and polymethacrylic acid. Insolubilization can be effected by ionizing radiation or chemical cross-linking. The gel must be capable of retaining relatively large quantities of a liquid. Water can be employed as the sole liquid, other liquids such as alcohols can be used, or mixtures of water and other liquids or solutes can be employed. When it is desirable to use more than one gel layer, a thin film of an inert material such as polyethylene or a metal foil is used to separate the gel layers and thereby effectively prevent adhesion of the layers when stacked.

The Herrett et al patent pertains to a plant growth medium containing an active agent and a water-insoluble, cross-linked polymeric material that serves as a matrix for the active agent. The polymeric material is illustratively polyvinyl alcohol, PVP, polyacrylic acid, polyvinyl acetate, polyacrylamide, and a copolymer of vinyl alcohol and vinyl acetate. The polymeric material is cross-linked either chemically or by ionizing radiation. Irradiation is carried out in the solid phase or in solution using water, for example, as the solvent. In one embodiment, a homogeneous water solution of the polymeric material is prepared and then irradiated for a period of time sufficient to cause the formation of a gel-like material, and the gel-like material is dewatered. Exemplary active agents are quaternary ammonium salts, copper sulfate, antibiotics and propylene glycol insect repellants. At column 10, lines 39-44, it is said that the roots of plants grown in soil formulations containing the cross-linked poly(ethylene oxide) of Herrett et al had adhered thereto particles of the polymeric matrix.

The Sohl patent is concerned with an adhesive tape having a water-soluble adhesive composition that is essentially a blend of a solid water-soluble polyvinyl carboxylic acid such as polyacrylic acid, and a compatible hydroxy-polyalkylene permanent elasticizer such as polyethylene glycol or polypropylene glycol. Another exemplary polyvinyl carboxylic acid is a 50/50 copolymer of polyvinyl methyl ether and maleic anhydride. Internal strength of the adhesive is increased by including in the adhesive mixture a chemical cross-linking agent. The cured type of adhesive is said to be more resistant to water but to dissolve in water when mechanically agitated or mixed.

Other prior art patents that in addition to the Morse and Herrett patents discussed above, pertain to a hydrogel based upon N-vinyl-2-pyrrolidone include U.S. Pat. No. 3,878,175 to Steckler, U.S. Pat. No. 3,759,880 to Hoffmann et al and U.S. Pat. No. 4,226,247 to Hauser et al. The Steckler patent is concerned with a highly spongy polymeric material characterized by swelling in water and being soft when wet. This spongy polymer is prepared by simultaneously copolymerizing and partially cross-linking 30–90 weight percent of an N-vinyl lactam monomer and 10–70 weight percent of an acrylate monomer. The spongy material is said to be adaptable for industrial applications, human use in toiletry, and as a sterile surgical dressing for sponging, wiping, or absorbing pus, blood and other body fluids during surgical operations. The Hoffman et al patent relates to the manufacture of insoluble and only slightly swellable poly-N-vinylpyrrolidone-2. The polymeric material of this patent is said to be a valuable absorbant for many purposes, especially as a beverage clarifying agent. The Hauser et al patent relates to an electrode having an adhesive that is preferably PVP-based. The adhesive is compounded by mixing with an active agent such as PVP, a plasticizer such as dioctyl phthalate, camphor or glycerin, and, alternatively, a conventional tackifier.

The Herrett et al, Yamauchi et al and Morse patents, discussed above, describe the use of radiation to cross-link a polymeric material. Similarly, U.S. Pat. No. 3,897,295 to Dowbenko, U.S. Pat. No. 3,264,202 to King, U.S. Pat. No. 2,964,455 to Graham, U.S. Pat. No. 3,841,985 to O'Driscoll et al, and U.S. Pat. No. 4,115,339 to Restaino pertain to the irradiation of polymeric materials.

In the Dowbenko et al patent, a solventless or nearly solventless solution of a polymer in a monomer is irradiated. The King patent pertains to forming a gel-like material by treating polymers of ethylene oxide with radiation. The gel-like material of this patent is said to have utility as a humidifier.

The O'Driscoll et al patent is concerned with irradiation of a solid, dry material containing PVP, and the Graham patent relates to the use of irradiation to modify solid articles made from polymeric alkylene oxides and polyvinyl ethers. At column 3, lines 59–61 of the Graham patent, it is disclosed that a benzene-soluble polytetramethylene oxide was soaked in water prior to irradiation. In the Restaino patent, an aqueous solution of a water-soluble vinyl monomer is irradiated for the purpose of forming high molecular weight water-soluble polymers.

I believe this prior art and the other prior art of which I am aware, fails to provide a novel water-insoluble, hydrophilic, elastomeric, pressure-sensitive adhesive that is transparent, ultraconformable and a soft, but strong, rubber-like solid that will absorb moisture that cannot be squeezed out; that will transmit oxygen, moisture, and drugs or salts soluble in the adhesive; and that will serve as a barrier to bacteria.

This adhesive could be useful as a coating on a supportive web-like substrate. The adhesive-coated web-like substrate could be used as a bandage, a burn or wound dressing, an ostomy device, a decubitus ulcer pad, a sanitary napkin, a diaper, a vibration or impact absorbing material such as a padding in shoes, splints, casts and orthopedic devices or an athletic padding, a sound absorbing material, or a medium for delivering a pharmacologically active agent. Additionally, a self-supporting layer of this adhesive could serve these same uses, and furthermore be useful as a cosmetic face mask and to secure a prosthesis or article of apparel to a mammalian body. One type of the novel adhesive could be electroconductive and function to attach an electrically conductive member of an electrode to a selected surface such as mammalian tissue.

DISCLOSURE OF THE INVENTION

It is accordingly one object of the present invention to provide a novel water-insoluble, hydrophilic elastomeric, pressure-sensitive adhesive. This adhesive absorbs moisture that cannot be squeezed out; is transparent, ultra-conformable, and a soft, yet strong, rubber-like solid that serves as a barrier to bacteria; and transmits oxygen, moisture, and drugs or salts soluble in the adhesive.

A further object is to provide a supportive, web-like substrate coated with the adhesive.

A still further object is to provide a bandage, a wound or burn dressing, a sanitary napkin, a diaper, an ostomy device, a decubitus ulcer pad, a vibration or impact absorbing material, a sound absorbing material, and a medium for delivering a pharmacologically active agent having a layer of the adhesive supported by a web-like substrate.

An even further object is to provide a self-supporting layer of the adhesive that will serve these same uses, and furthermore be useful as a cosmetic face mask and to secure a prosthesis or article of apparel to a mammalian body.

A still further object is to provide a method for using the self-supporting layer of the adhesive for securing a prosthesis or article of apparel to a mammalian body.

A yet further object is to provide a method of making the adhesive.

An additional object of the present invention is to provide an adhesive of this type that is electroconductive and useful for attaching an electrically conductive member of an electrode to a selected surface such as mammalian tissue.

An even additional object is to provide an electrode having a layer of such an adhesive.

Another object is to provide a transcutaneous electric nerve stimulation electrode, an electrosurgical return electrode or an EKG monitoring electrode having a layer of such an adhesive.

Yet another object is to provide a method of adhering an electrode to mammalian tissue that includes contacting the tissue with an electrode of this type.

Other objects and advantages of the present invention will become apparent as the description thereof proceeds.

In satisfaction of the foregoing objects and objectives, there is provided by this invention a water-insoluble, hydrophilic, elastomeric, pressure-sensitive adhesive that includes at least one irradiation cross-linked synthetic organic polymer and an adhesive plasticizer. The adhesive plasticizer is present in an amount sufficient to maintain the elastomeric state of the adhesive. The cross-linked polymer is water-insoluble, has a three-dimensional matrix, and is formed from a solution or dispersion of at least one suitable gel-forming, uncrosslinked, synthetic organic polymer in a solubilizing plasticizer. The solubilizing plasticizer is irradiation cross-linking compatible, and the relative proportions of the uncrosslinked polymer and the solubilizing plasticizer are such that the gel formed upon irradiation cross-linking, retains the solubilizing plasticizer within the three-dimensional matrix. The plasticizers are the same or different, and include at least one substantially non-volatile elasticizer. The elasticizer is present in an amount sufficient to maintain adhesivity when the adhesive plasticizer is substantially the elasticizer. The adhesive is useful as a coating on an adhesive-supporting, web-like substrate, and is also useful as a self-supporting layer.

Also in satisfaction of the foregoing objects and objectives, there is provided by this invention a conductive, water-insoluble, hydrophilic, elastomeric pressure-sensitive adhesive. This adhesive includes at least one irradiation cross-linked synthetic organic polymer, a conductivity-enhancing amount of at least one conductivity-enhancing material, and an adhesive plasticizer. The adhesive plasticizer is present in an amount sufficient to maintain the elastomeric state of the adhesive. The cross-linked polymer is water-insoluble, has a three-dimensional matrix, and is formed from a solution or dispersion of at least one suitable gel-forming, uncrosslinked synthetic organic polymer in a solubilizing plasticizer. The solubilizing plasticizer is irradiation cross-linking compatible, and the relative proportions of the uncrosslinked polymer and the solubilizing plasticizer are such that the gel formed upon irradiation cross-linking, retains the solubilizing plasticizer within the three-dimensional matrix. The plasticizers are the same or different, and include at least one substantially non-volatile elasticizer. The elasticizer is present in an amount sufficient to maintain adhesivity when the adhesive plasticizer is substantially the elasticizer. Also provided by the present invention is an electrode that includes an electrically conductive member and the electro-conductive adhesive. Furthermore, in accordance with the present invention, there is provided a method of adhering an electrode to mammalian tissue that includes contacting the tissue with this electrode.

BRIEF DESCRIPTION OF THE DRAWING

Reference is hereby made to the accompanying drawing, which forms a part of the specification of the present invention.

BEST MODE FOR CARRYING OUT THE INVENTION

As discussed above, the present invention pertains to a novel pressure-sensitive adhesive. This adhesive is a water-insoluble, hydrophilic, elastomeric, pressure-sensitive adhesive; is a soft, yet strong, rubber-like solid; and is further characterized by being transparent and ultraconformable. In fact, my adhesive has much higher drape than the skin itself. My adhesive absorbs moisture that cannot be squeezed out, transmits oxygen, moisture, and drugs or salts soluble in the adhesive, and functions as a barrier to bacteria.

My adhesive adheres aggressively to skin but does not appear to stick well to hair, thus eliminating or greatly reducing the discomfort that frequently accompanies removal of a pressure-sensitive adhesive coated substrate from an area of human body having hair present. My adhesive can be left on the human body several hours or even days, and discoloration and wrinkled appearance of the skin does not result.

My adhesive can absorb a significant amount of moisture without significant reduction in adhesion, and in this regard will absorb or transmit perspiration as it leaves the skin surface including moisture, salt, urea, ammonia and other waste products. My adhesive can be prepared to contain a significant amount of water, or can be prepared in a dehydrated state and thus have even greater capability for absorbing moisture. My "dry" adhesive, as illustrated in Example 1 and Table 1, has unexpected high oxygen permeance (the meaning of the term "dry" is explained below). The presence of a significant water phase in the adhesive is expected to produce even higher oxygen permeability.

In most embodiments, my adhesive is suberabsorbant. By superabsorbant, I mean that the adhesive will absorb an amount of water equal to approximately its own weight, without a loss in adhesivity. Exemplary embodiments in which the adhesive is not superabsorbant exist when the plasticizer is substantially 2 ethyl, 1-3 hexanediol or triethyl citrate, or mixtures thereof. In most of the uses for the adhesive set forth in this description of my invention, it is advantageous that the adhesive is superabsorbant. However, when used as an ostomy adhesive or possibly when used as a drug delivery medium (depending on the solubility characteristics of the drug), the adhesive should be absorbant, not superabsorbant, and thus plasticizers of the type just mentioned should be used.

My adhesive will filter out microorganism contaminants by presenting a tortuous path for the influx of the bacteria. As a result, antibiotics in a wound dressing may be unnecessary in most cases. My adhesive so closely matches the fluid transmission and bacteria barrier characteristics of human skin as to be like an instantly healing injury as far as infection is concerned. It is believed that scar tissue formation would be retarded.

Figure 1:
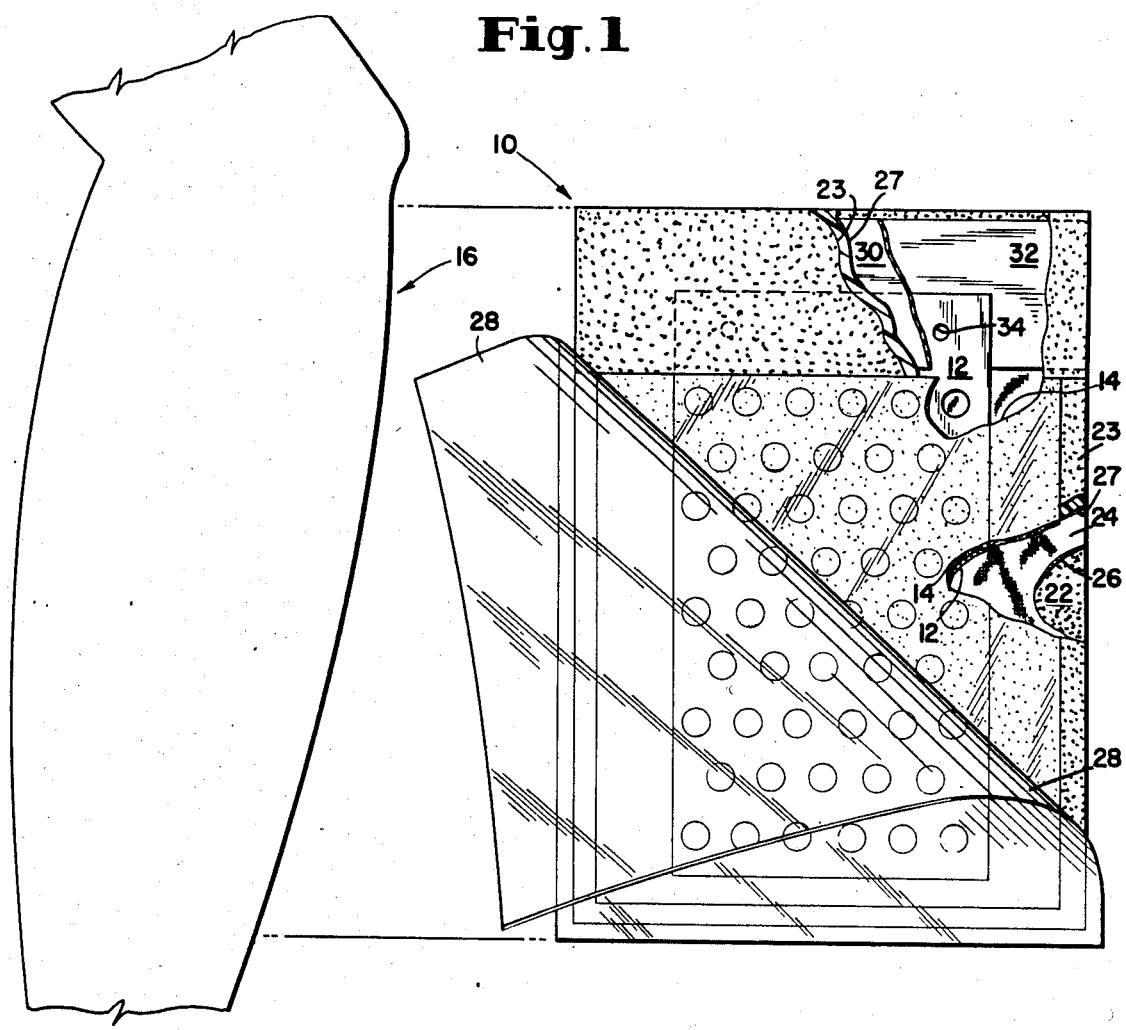
FIG. 1 shows an electrosurgical return electrode (with certain areas cut away) having a layer 14 of an electroconductive, water-insoluble, hydrophilic, elastomeric, pressure-sensitive adhesive, with a portion of release liner 28 peeled back for attaching to arm 16.

In one embodiment, the adhesive is electroconductive and is particularly suitable for use with an electrode. Referring to FIG. 1, there is illustrated an electrosurgical return pad 10 that includes a conventional electrically conductive member 12 and an electroconductive, water-insoluble, hydrophilic, elastomeric, pressure-sensitive adhesive 14, in accordance with the invention. Also shown in this Figure is an arm 16, which serves as a surface to which electrosurgical return pad 10 is attached.

Figures 2, 3:
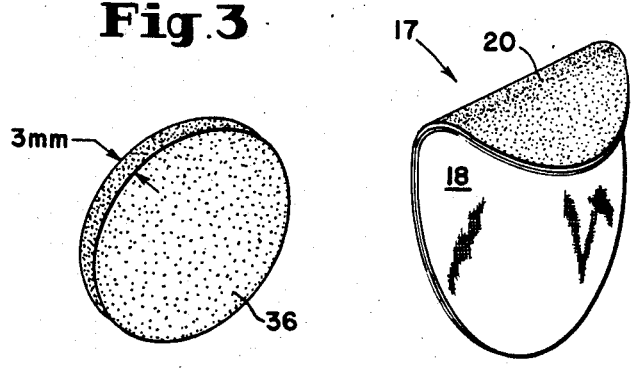
FIG. 2 depicts a supportive web-like substrate 18 with a layer 20 of a water-insoluble, hydrophilic, elastomeric pressure-sensitive adhesive coated thereon.
FIG. 3 shows a self-supporting layer 36 of the adhesive of FIG. 2.

Referring to FIG. 2, there is shown a bandage 17 having a supportive web-like substrate 18 and an adhesive layer 20, in accordance with the invention, coated thereon. This general structure is typical of a bandage, sanitary napkin, burn or wound dressing, ostomy device, decubitus ulcer pad, diaper, a vibration or impact absorbing material such as a padding, a sound absorbing material, and a medium for delivering a pharmacologically active agent, in accordance with the invention. However, the size and thickness of substrate 18 and adhesive layer 20 will vary depending upon the use selected.

Also shown in FIG. 1 are foam layers 22 and 23, non-woven fabric layer 24, adhesive layers 26 and 27, release liners 28, 30 and 32, and electrical connection holes 34. These aspects of the pad are conventional. Adhesive layer 26 serves to bond fabric layer 24 to foam layer 22. Foam layer 22 is conveniently a polyethylene foam, and fabric layer 24 is suitably a polyester material such as Nexus ® polyester material sold by Burlington. Pad 10 is attached to arm 16 after release liner 28 is removed.

Pad 10 is advantageously manufactured in part by coating foam layer 22 with adhesive layer 26, laying down fabric layer 24 on the adhesive to form a laminate, placing conductive member 12 on fabric layer 24, applying a solution or dispersion of an uncrosslinked, appropriate synthetic organic polymer in a suitable plasticizer to fabric layer 24 and conductive member 12, and subjecting the resulting laminate to ionizing radiation. Release liner 28 is then put into place. The synthetic organic polymer and plasticizer are described below.

Referring to FIG. 3, there is shown a self-supporting layer 36 of the adhesive of the present invention. This general structure is typical for all uses of the adhesive as a self-supporting layer. However, the size and thickness of layer 36 will vary depending upon the use selected. Preferably, a self-supporting layer of the adhesive ranges in thickness from about 3–6 mm. When prepared for use as a self-supporting layer, the adhesive layer, of course, could be sandwiched between a pair of conventional release liners.

My adhesive includes at least one irradiation cross-linked synthetic organic polymer and a sufficient amount of an adhesive plasticizer to maintain the elastomeric state of the adhesive. The cross-linked polymer is formed by dispersing or solubilizing at least one suitable gel-forming, uncrosslinked synthetic organic polymer in a plasticizer that has a composition the same as or different than the adhesive plasticizer, and then subjecting the resulting solution or dispersion to an appropriate dosage of irradiation. Use of an appropriate dosage of irradiation produces an adhesive with the properties described herein. The cross-linked polymer of the adhesive is water-soluble and has a three-dimensional matrix.

Conveniently, the uncrosslinked synthetic organic polymer includes repeating units derived from a carboxy vinyl monomer, a vinyl ester monomer, an ester of a carboxy vinyl monomer, a vinyl amide monomer, a hydroxy vinyl monomer, a cationic vinyl monomer containing an amine or a quaternary ammonium group, or an N-vinyl lactam monomer. Alternatively, the uncrosslinked polymer is conveniently a homopolymer or copolymer of a polyvinyl ether, or a copolymer derived from a half ester of maleic anhydride. A polymer formed from a compatible monomer mixture may be used such as a polymer formed from a mixture of an N-vinyl lactam monomer and an ester of a carboxy vinyl monomer. Also, compatible uncrosslinked polymers may be used, in appropriate amounts, such as about 11.25 weight percent polyvinyl alcohol (88% hydrolyzed) and about 3.75 weight percent polyacrylic acid having a molecular weight of about 450,000. Advantageously, the uncrosslinked polymer is water-soluble, and includes, for example, repeating units derived from a carboxy vinyl monomer, is a homopolymer or copolymer of a polyvinyl alcohol, or is a copolymer formed from approximately substantially equal amounts of methyl vinyl ether and maleic anhydride.

Preferably, the uncrosslinked polymer includes repeating units derived from an N-vinyl lactam monomer.

Illustrative N-vinyl lactam monomers are N-vinyl-2-pyrrolidone, N-vinyl-ε-caprolactam and mixtures thereof. The N-vinyl lactam monomer is suitably either a homopolymer of N-vinyl-2-pyrrolidone, or a copolymer of N-vinyl-2-pyrrolidone and at least one vinyl monomer that is compatible with solubility or dispersability of the uncrosslinked copolymer in the solubilizing or dispersing plasticizer and that is compatible with solubility or dispersability of the cross-linked copolymer in the adhesive plasticizer. Vinyl monomers of this type include vinyl acetate, and an ester of an $\alpha,\beta$-olefinically unsaturated carboxylic acid and an amino group-containing alcohol. When the vinyl monomer is vinyl acetate, the mole ratio of vinyl acetate and N-vinyl-2-pyrrolidone is advantageously such that the copolymer is water-soluble.

A copolymer of N-vinyl-2-pyrrolidone and the carboxylic acid ester is preferred, with the copolymer suitably containing mole percent of the ester. It is particularly preferred for the ester to be either dimethylaminoethyl methacrylate or the partially or fully quaternized salt of this methacrylate. A partially quaternized salt-containing copolymer of N-vinyl-2-pyrrolidone (having a K value of approximately 90) is sold as a 20% aqueous solution under the trademark Gafquat 755 N. This commercially available copolymer contains 20 mole percent of dimethylaminoethyl methacrylate partially quarternized with diethyl sulfate. An advantageous polyvinyl pyrrolidone is K-90 PVP, and is available from GAF as Type NP-K90.

For purposes of this specification, the term "carboxy vinyl monomer" includes a water-soluble salt of a carboxy vinyl monomer with, for example, an alkali metal, ammonia or an amine. Exemplary carboxy vinyl monomers include acrylic acid, methacrylic acid, crotonic acid, isocrotonic acid, itaconic acid and anhydride, a 1,2-dicarboxylic acid such as maleic acid or fumaric acid, maleic anhydride, and mixtures thereof. Conveniently, the carboxy vinyl monomer is acrylic acid.

When the carboxy vinyl monomer is a 1,2-dicarboxylic acid or maleic anhydride, the uncrosslinked polymer includes a comonomer. The comonomer is, for example, a $C_2$–$C_4$ olefinic monomer such as ethylene, propylene, n-butylene or isobutylene; a $C_4$ diolefinic monomer such as butadiene; a $C_1$–$C_4$ alkyl vinyl ether such as methyl vinyl ether; styrene; or vinyl acetate. The amount of the 1,2-dicarboxylic acid or maleic anhydride is substantially equivalent, on a molar basis, to the amount of the comonomer. Vinyl acetate is a suitable comonomer in an amount up to as much as about 20 weight percent, with any of the other carboxy vinyl monomers.

As the polyvinyl alcohol, one or more water-soluble polyvinyl alcohols are used. A convenient polyvinyl alcohol is a high molecular weight, 88% hydrolyzed polyvinyl alcohol prepared through hydrolysis of polyvinyl acetate. This polyvinyl alcohol is commercially available as Gelvatol ® 20–90 and is a product of Monsanto.

The irradiation cross-linked polymer is produced by carrying out the irradiation on a solution or dispersion of the suitable gel-forming, uncrosslinked synthetic organic polymer in a plasticizer that is water-soluble or water-dispersible, into which the uncrosslinked polymer can be dissolved or dispersed, and into which water and the uncrosslinked polymer can be dissolved or dispersed. The term "solubilizing plasticizer" is used in this description to designate this plasticizer. This plasticizer is irradiation cross-linking compatible. For purposes of this specification, the term "irradiation cross-linking compatible" means that the solubilizing plasticizer does not inhibit irradiation-caused cross-linking of the polymer.

The solubilizing plasticizer includes at least one substantially non-volatile elasticizer, and conveniently includes a volatile solvent that in combination with the elasticizer serves to disperse or dissolve the polymer. The volatile solvent is either aqueous, non-aqueous, or a mixture, and is selected in conjunction with the elasticizer to form a plasticizer composition into which the uncrosslinked polymer can be dissolved or dispersed, and to form an adhesive plasticizer that will dissolve or disperse the cross-linked polymer. Conveniently, the volatile solvent is aqueous, and it is especially convenient for the volatile solvent to be water. When the volatile solvent is water, up to about 90% of the solubilizing plasticizer may be water. A very important feature that separates my unique adhesive from the prior art is that certain formulations retain its adhesivity upon removal of the volatile solvent. In contrast, an aqueous solvent gel such as disclosed by Steckler, Herrett et al, and Kater will become hard and non-adhesive upon removal of the volatile solvent.

The substantially non-volatile elasticizer is present in an amount sufficient to maintain adhesivity of the cross-linked polymer-containing adhesive when the adhesive plasticizer is substantially made up of the elasticizer. By "substantially" in reference to the plasticizer is meant that only as much as about 2 weight percent of the volatile solvent is present. Advantageously, the elasticizer is present in an amount ranging from about 0.5 to 4:1, on a weight basis, of the cross-linked polymer.

The solution or dispersion formed from combining the uncrosslinked polymer with the solubilizing plasticizer is either clear or hazy in appearance. The relative proportions of the uncrosslinked polymer and the plasticizer are such that the gel formed upon irradiation crosslinking, retains this plasticizer within the three-dimensional matrix.

Conveniently, the substantially non-volatile elasticizer is a suitable polyhydric alcohol, mono- or diether of a polyalkylene glycol, mono- or diester of a polyalkylene glycol, imidazoline derivative amphoteric surfactant, lactam, N-substituted lactam, amide, polyamide, amine, polyamine, condensate of polyethylene imine with epichlorohydrin, polyquaternary ammonium compound or compatible mixture thereof. The polyhydric alcohol is used with particular advantage, and it is very advantageous that the polyhydric alcohol is a polyalkylene glycol, in particular a polyethylene glycol. Other useful polyhydric alcohols include sorbitol, 1,3-butane diol, 1,4-butane diol, 1,4-butene diol, a suitable corn sugar derivative, pentaerythritol, trimethylolethane, glycerine, propylene glycol, 1,3-propane diol, polyglycerine, ethylene glycol, and compatible mixtures. It is necessary that the elasticizer present during the irradiation treatment step is irradiation cross-linking compatible. Thus, for example, glycerine, which tends to reduce the effectiveness of irradiation cross-linking, should not be present as the elasticizer prior to irradiation treatment in an amount greater than about 5% of the total formula weight, depending upon the polymer upon which the adhesive is based. This amount of glycerine can be present as the elasticizer and can accordingly be added to the elasticizer, once the cross-linking step has been completed. It is to be understood that, if, for example, the elasticizer is the amide or amine, the amide or amine is substantially non-volatile. Also, as explained below, the elasticizer is typically a liquid at room temperature.

Once the irradiation treatment is completed, another way of altering the composition of the adhesive plasticizer in those cases in which this plasticizer contains a volatile solvent, is to remove some of the volatile solvent. When the volatile solvent is water, it is preferable to remove some of the water so that only a small amount, say up to about 5%, of water is present as part of the adhesive plasticizer. In fact, it is even more preferable to remove a sufficient amount of water so that the adhesive is "dry", as defined below. An advantage of these dewatered adhesives is their capability for greatly increased moisture absorption. Additionally, as shown in the Examples, the dewatered or "dry" adhesive is superior in its adhesivity to the "wet" adhesive, has markedly superior water vapor transmission, and has unexpectedly high oxygen permeance. By "dry", for purposes of this specification, is meant that an adhesive has a degree of dryness that is minimally that produced by allowing an adhesive to air dry for about 48 hours at approximately 30% relative humidity and 20° C. By "wet", for purposes of this specification, is meant that the adhesive contains at least about 55% water.

Generally, as noted above, the elasticizer is a liquid at room temperature. However, it is possible for the elasticizer to be a solid at room temperature when a freezing point depression results from the combination of the elasticizer with the uncrosslinked polymer, some other component of the solubilizing plasticizer, or a suitable additive material that is placed into the formulation prior to the cross-linking step. A material that is normally solid but that experiences freezing point depression in the presence of an appropriate uncrosslinked polymer such as polyacrylic acid having a molecular weight of approximately 450,000, is a polyethylene glycol having a molecular weight from about 600 to about 20,000. Particularly advantageous polyethylene glycols, for use in my invention, have a molecular weight of about 300 or about 600. A polyethylene glycol (PEG) having a molecular weight of 300 is sold by Union Carbide under the trademark Carbowax 300, and a PEG having a molecular weight of 600 is sold under the trademark Carbowax 600. It is also possible for an elasticizer that is solid at room temperature to be used, if the remainder of the plasticizer composition is capable of solubilizing or dispersing both a mixture of this and the uncrosslinked polymer, and a mixture of this and the cross-linked polymer.

As discussed, the elasticizer is illustratively the polyhydric alcohol, the mono- or diether of a polyalkylene glycol or the N-substituted lactam. It is very advantageous when the polyhydric alcohol is a polyalkylene glycol, with polyethylene glycol, polypropylene glycol and the copolymer of ethylene oxide and propylene oxide being exemplary of polyalkylene glycols. A mono- or diether of polyethylene glycol is suitably the mono- or diether of a polyalkylene glycol, and a polyethoxylated fatty alcohol, polyethoxylated nonyl phenol or a polyethoxylated octyl phenol is conveniently the monoether of the polyethylene glycol. Illustrative N-substituted lactams include N-isopropyl-2-pyrrolidone, N-(N,N-dimethylamino)propyl-2-pyrrolidone, and N-cyclohexyl-2-pyrrolidone.

Suitably, the uncrosslinked polymer includes repeating units derived from a vinyl amide monomer. A particularly suitable monomer of this type is an amide of a α,β-olefinically unsaturated carboxylic acid, with acrylamide and dimethylaminopropyl methacrylamide being exemplary. Another amide of this type is methacrylamidopropyl trimethylammonium chloride.

As explained earlier, it is advantageous for the uncrosslinked polymer to include repeating units derived from a carboxy vinyl monomer. When the carboxy vinyl monomer is acrylic acid, the polymer may be a copolymer of acrylic acid and ethylene, vinyl acetate or an acrylate ester. With this copolymer, there is included an amount of a base sufficient to solubilize the polymer, with the base being an amine, a quaternary ammonium or an alkali metal hydroxide. When the carboxy vinyl monomer is maleic acid, an advantageous comonomer is methylvinyl ether, ethylene, vinyl acetate, styrene or butadiene, with the amount of the comonomer being substantially equivalent, on a molar basis, to the amount of the maleic acid. When the comonomer is styrene or vinyl acetate, there is included enough of a base sufficient to solubilize the copolymer.

An adhesive in accordance with my invention prepared from an uncrosslinked polymer or plasticizer that is skin irritating, or that otherwise contains a skin-irritating additive is better employed so as not to be in contact with skin. An exemplary polymer of this type predominantly includes repeating units derived from a carboxy vinyl monomer such as acrylic acid, and an illustrative plasticizer contains a surfactant or detergent as the elasticizer. Otherwise, my adhesive has the substantial advantage of being hypoallergenic.

When the uncrosslinked polymer includes repeating units derived from an N-vinyl lactam monomer, particularly useful elasticizers include a polyethylene glycol, an imidazoline derivative amphoteric surfactant, a polyethoxylated fatty alcohol, a polyethoxylated fatty acid, a polyethoxylated nonyl phenol, and a polyethoxylated octyl phenol. A polyethoxylated octyl phenol surfactant is sold under the Triton brandname by Rohm & Haas.

A convenient polyvinyl ether for use as the uncrosslinked polymer starting material is polymethylvinyl ether or polyethyl vinyl ether. Particularly suitable elasticizers include the monoether of a polyalkylene glycol or the monoester of a polyalkylene glycol. An illustrative monoether of a polyalkylene glycol is polyethoxylated octyl phenol, and an exemplary monoester of a polyalkylene glycol is a fatty acid ester of polyethylene glycol such as polyethylene glycol 300 monostearate. Other useful elasticizers include an N-substituted lactam and, of course, polyethylene glycol. An N-substituted lactam is also a particularly convenient elasticizer for use with an uncrosslinked polymer derived from an N-vinyl lactam monomer.

When the uncrosslinked polymer includes repeating units derived from a vinyl ester monomer, the polymer contains an amount of a second comonomer sufficient to make the polymer soluble or dispersible in the plasticizer prior to the irradiation treatment step, and also soluble in the adhesive plasticizer. Exemplary vinyl esters include vinyl acetate and vinyl propinate, and the comonomer is illustratively an N-substituted lactam, a vinyl alcohol, a hydrolyzed maleic anhydride, or crotonic acid. A copolymer containing the vinyl ester and vinyl alcohol may be prepared through incomplete hydrolysis of the vinyl ester. A copolymer of vinyl acetate and maleic anhydride is prepared through hydrolysis and base treatment. When the comonomer is crotonic acid, a sufficient amount of an appropriate base is added to dissolve the polymer in the plasticizer prior to the irradiation treatment. Conveniently, this copolymer contains vinyl acetate and crotonic acid in an about 19:1 mole ratio.

When the uncrosslinked polymer is a copolymer derived from a half ester of maleic anhydride, the half ester is suitably the methyl half ester or the ethyl half ester, and the comonomer is advantageously a $C_1$-$C_4$ vinyl ether such as methyl vinyl ether, or ethylene.

Other exemplary vinyl amide monomers are prepared from an α,β-olefinically unsaturated carboxylic acid and a diamine such as dimethylaminoethylamine and aminoethyl trimethylammonium chloride. Illustrative hydroxy vinyl monomers, for use as the uncrosslinked polymer starting material, include hydroxyethyl acrylate and hydroxypropyl acrylate. Vinyl benzyl trimethylammonium chloride exemplifies a cationic vinyl monomer containing an amine or a quaternary ammonium group.

As explained earlier, the relative proportions of the uncrosslinked polymer and the solubilizing plasticizer are such that the gel formed upon the irradiation crosslinking, retains this plasticizer within the three-dimensional matrix. When the uncrosslinked polymer includes repeating units derived from a carboxy vinyl monomer, a vinyl ester monomer, an ester of a carboxy vinyl monomer, a vinyl amide monomer, a hydroxy vinyl monomer, or a cationic vinyl monomer containing an amine or a quaternary ammonium group, the solution or dispersion to be irradiated conveniently contains about 5–50 weight percent of the uncrosslinked polymer. Also, when the uncrosslinked polymer is a copolymer derived from a half ester of maleic anhydride, the solution or dispersion advantageously contains about 5–50 weight percent of the uncrosslinked polymer. It is suitable for the solution or dispersion to contain about 7–60 weight percent of the uncrosslinked polymer, in the case that the uncrosslinked polymer includes repeating units derived from an N-vinyl lactam monomer. When the uncrosslinked polymer is a homopolymer or copolymer of a polyvinyl ether, it is convenient for the solution or dispersion to contain about 5–60 weight percent of the uncrosslinked polymer. In the case where the uncrosslinked polymer is a homopolymer or copolymer of a polyvinyl alcohol, the solution or dispersion to be irradiated advantageously contains about 5–30 weight percent of the uncrosslinked polymer. When the uncrosslinked polymer includes repeating units derived from a carboxy vinyl monomer, it is especially suitable for the solution or dispersion to contain about 14–20 weight percent of the uncrosslinked polymer, with about 20 weight percent being preferred. When the uncrosslinked polymer includes repeating units derived from an N-vinyl lactam monomer, it is particularly advantageous for the solution or dispersion to contain about 12.5–22.5 weight percent of the uncrosslinked polymer, with about 20 weight percent again being preferred. A particularly convenient concentration of the uncrosslinked polymer in the solution or dispersion is about 7–25 weight percent when the uncrosslinked polymer is a homopolymer or copolymer of a polyvinyl alcohol, with about 10 weight percent being preferred.

When the uncrosslinked polymer includes repeating units derived from a carboxy vinyl monomer, a particularly suitable ratio of the elasticizer to the carboxy vinyl monomer is an about 1:1 ratio, on a weight basis. When the uncrosslinked polymer is polyacrylic acid, the polyacrylic acid conveniently has a molecular weight of about 450,000–500,000. Polyacrylic acid having a molecular weight of about 500,000 is sold in a 15% aqueous solution by B. F. Goodrich as Carbopol ® Ex-17, and polyacrylic acid having a molecular weight of 450,000 is sold as Carbopol ®907. A particularly advantageous adhesive, as discussed earlier, is "dry". Removal of the volatile solvent to form this adhesive is achieved as explained above, or by using equivalent techniques.

When the adhesive includes irradiation cross-linked K-90 polyvinyl pyrrolidone and polyethylene glycol having a molecular weight of about 300, it is highly preferred for the polyethylene glycol to be present in an amount that is about 0.75–1.5 times the amount, on a weight basis, of the polyvinyl pyrrolidone. These particular compositions and similar compositions in which the polyvinyl pyrrolidone is a copolymer of N-vinyl-2-pyrrolidone and vinyl acetate or either dimethylaminoethyl methacrylate or the partially quaternized salt of this methacrylate, are the very preferred compositions of this invention.

The dosage of irradiation to produce my adhesive depends upon factors that include the concentration of the uncrosslinked polymer in the solubilizing plasticizer, and the molecular weight of the uncrosslinked polymer. For instance, a relatively lower dosage of irradiation is required by a relatively higher concentration of the uncrosslinked polymer or a relatively higher molecular weight uncrosslinked polymer; whereas a relatively higher amount of irradiation is required by a relatively lower concentration of the uncrosslinked polymer or a relatively lower molecular weight uncrosslinked polymer. The choice of elasticizer and the relative proportions of the elasticizer, the remaining plasticizer components, and the uncrosslinked polymer also affect the dosage requirements.

In addition, when the irradiation is carried out at a relatively low rate, and in the presence of a free radical scavenger such as oxygen, relatively higher dosages are required; whereas, when the irradiation is carried out under conditions that favor the relatively long existence of the free radicals produced, as for example, when the irradiation is carried out with a high dose rate, in the absence of oxygen, or in solution where oxygen is rapidly used up, a relatively lower dosage is necessary.

The term "irradiation" as used herein, means high energy radiation and/or the secondary energies resulting from conversion of electron or other particle energy to neutron or gamma radiation. These energies are at least equivalent to about 100,000 electron volts. While various types of irradiation are suitable for this purpose, such as X-ray and gamma and beta rays, the radiation produced by accelerated high energy electrons is conveniently and economically applicable. However, regardless of the type of radiation and the types of equipment used for its generation or application, the ionization radiation need only be equivalent to at least about 100,000 electron volts.

While there is no upper limit to the electron energy that can be applied advantageously, the effects desired in the practice of this invention can be accomplished without having to exceed about 20 million electron volts. Generally, the higher the electron energy used, the greater is the depth of penetration into the structure of the materials to be treated, and the shorter is the time of exposure required. For other types of radiation, such as gamma and X-rays, energy systems equivalent to the above range of electron volts are desirable.

It is intended that the term "irradiation" include "ionizing radiation" which has been defined as radiation possessing an energy at least sufficient to produce ions or to break chemical bonds and thus includes "ionizing particle radiation" as well as radiations of the type termed "ionizing electromagnetic radiation".

The term "ionizing particle radiation" has been used to designate the emission of electrons or highly accelerated nuclear particles such as protons, neutrons, alpha-particles, deuterons, or beta-particles, directed in such a way that the particle is projected into the mass to be irradiated. Charged particles can be accelerated by the aid of voltage gradients by such devices as accelerators with resonance chambers, Van der Graaff generators, betatrons, synchrotons, cyclotrons, dynamatrons and insulated core transformers. Neutron radiation can be produced by bombarding a selected light metal such as beryllium with positive particles of high energy. Particle radiation can also be obtained by the use of an atomic pile, radioactive isotopes or other natural or synthetic radioactive materials.

"Ionizing electromagnetic irradiation" is produced when a metallic target, such as tungsten, is bombarded with electrons of suitable energy. This energy is conferred to the electrons by potential accelerators of over 0.1 million electron volts. In addition to irradiation of this type, commonly called X-ray, an ionizing electromagnetic irradiation suitable for the practice of this invention can be obtained by means of a nuclear reactor (pile) or by the use of natural or synthetic radioactive material, for example, cobalt 60.

Dosages of irradiation ranging from about 0.5–7.5 megarads are useful for cross-linking the uncrosslinked polymer, with a dosage of about 3.5–4.5 megarads being particularly suitable. Thus, this dosage range is especially useful for a composition substantially containing about 18–22 weight percent, K-90 polyvinyl pyrrolidone, about 10–70 weight percent polyethylene glycol having a molecular weight of about 300, and water. The adhesive produced is a preferred adhesive, and can be made electro-conductive by including an appropriate amount of a conductivity enhancer such as about 6–8 weight percent. It is very preferred for this adhesive to contain about 25–30 weight percent of PEG 300, and about 20 weight percent PVP.

My adhesive optionally contains a compatible preservative such as methyl paraben or propyl paraben. Mixtures of preservatives may be used, and, when used, a preservative is used in an amount sufficient to achieve a preservative effect. Also, my adhesive may contain a pigment such as ultramarine blue.

My adhesive is useful as a coating on a supportive web-like substrate. As a result of high cohesion, and by a judicious choice of the web-like substrate so that there is a very high adhesion of the adhesive to the substrate, my adhesive does not leave behind an adhesive residue. When polystyrene, for example, is used as the supportive substrate, very high adhesion of the adhesive to the polystyrene results if irradiation is carried out with the solution or dispersion of the uncrosslinked polymer in direct contact with polystyrene.

A particular advantage of my adhesive is that it tends to be re-applicable. As a result, the adhesive may be re-positioned several times without loss of adhesive performance.

My adhesive is elastomeric and undergoes elastic deformation. When my adhesive is strained, a restoring static stress develops. Even after undergoing several hundred percent strain, there is little if any visually detectable permanent set, after relaxation of my adhesive. My adhesive is very low in stiffness and has a modulus as low as gelatin desserts or even lower.

Since my adhesive is elastomeric and does not exhibit excessive cold flow, it is possible to produce my adhesive in a very thick layer form, even as great as about 40 mm or more. However, a layer having a thickness of about 3–6 mm is preferable, especially when a layer of my adhesive is self-supporting, and has the advantage of allowing articulation of a patient's body with a minimum of retriction and a minimum of painful pulling. A self-supporting layer of my adhesive could be a coating on a non-supportive thickness of a web-like substrate such as gauze or a non-woven fabric. In this instance, the web-like substrate would function to increase dimensional stability and enable the adhesive to be cut more easily.

A supportive web-like substrate coated with a layer of my adhesive has a multiplicity of uses, and the web-like substrate is selected according to the desired use. Suitably, the web-like substrate is non-conductive. A number of uses exist for the coated substrate such as a bandage, a burn or wound dressing, a sanitary napkin, an ostomy device, a diaper, a decubitus ulcer pad, a vibration or impact absorbing material, a sound absorbing material, and a medium for delivering an adhesive-soluble pharmacologically active agent. In certain of these uses, the adhesive includes a pharmacologically active agent that is soluble in the adhesive.

When used as a self-supporting layer, my adhesive has the uses described above for the coated substrate. A self-supporting layer of my adhesive is also useful as a cosmetic face mask, and to secure a prosthesis or an article of apparel to a mammalian body.

When used in a bandage, my adhesive material is able to replace all three parts of the bandage, that is, the adhesive, gauze and substrate, and may be the best material known for any of these three parts. As the adhesive part of the bandage, it is non-traumatic, does not pull hair, does not induce painful pulling in use, does not cause discomfort or injury upon removal, and does not cause the skin-wrinkling moisture retention observed with many other adhesives. As a gauze material, my adhesive allows continual observation of a patient's condition without disturbing the patient. Being a soft elastomer, it provides superior padding as well. Being nonfibrous, it does not strongly adhere to a scab, and usually will be removed without scab trauma. My adhesive will significantly reduce bacterial influx by filtering bacteria out. Being elastomeric in nature, my adhesive can be used without a supporting substrate when an appropriate thickness is provided. Its superior drape will allow it to conform to the most intricate body contours, remaining attached even during vigorous movement. Its high oxygen and moisture permeability is most beneficial in bandage applications, particularly as a means of controlling anaerobic bacterial infection.

My adhesive can absorb the fluid exuded from a minor injury and thus serve as both adhesive and absorbant pad. A substantial advantage of this is that if an appropriately-sized sheet of adhesive-coated substrate is available, one can cut a special size or shape of bandage to fit the exact need. This is in contrast to commercially available bandages that are made of an absorbant pad secured to an adhesive tape, and that require providing a gauze pad of appropriate size and shape and also an adhesive tape of appropriate size and shape.

When gauze is used to cover an injury site, a frequent problem is that the coagulated blood and body fluids tend to encapsulate the gauze fibers, as a result of which the gauze becomes adhered to the injury site. In contrast, my adhesive is less likely to adhere to the injury. When used as a gauze replacement, my adhesive can be prepared to contain an amount of moisture ranging from about zero to ninety percent so that one can maintain either a high moisture environment or a low moisture environment over the area being treated.

As a burn dressing, it is believed my adhesive will function as an artificial skin graft that will stabilize a patient until grafts of his own tissue are available.

When used as sanitary napkin, a layer of my adhesive can serve as all three parts of the sanitary napkin, that is, as the absorbant material, the adhesive, and the supporting structural member. The ability of my adhesive to adhere to the contours of the vaginal area even during vigorous movement, to absorb menstrual fluid, and to provide a seal over the vaginal area makes this adhesive material an ideal sanitary napkin. An about 3/16" sheet of this material could be used alone, without support. When unsupported, the opposite side of the adhesive could have an undergarment adhesion-preventing coating provided, for example, by dusting this side with talc or treating it with a silicone fluid. Since may adhesive does not absorb particulates, it is advantageous to use a pad of another absorbant material over the center portion of the sanitary napkin.

As a cosmetic face mask, my adhesive is soft enough to be comfortably used over the entire face. Moisturizers could be added in an appropriate amount in order to provide an overnight beauty treatment which, being continuous through the night, will provide a most effective "youth restoring" beauty aid. Additionally, pharmacologically active agents such as those useful against acne or providing sunburn pain relief could be included in the adhesive.

When used as a delivery medium for a pharmacologically active agent, a layer of my adhesive can be applied to skin areas other than the face. This use is particularly advantageous when the pharmacologically active agent is able to pass through the skin. In addition to applying my adhesive to the skin, my adhesive may be located in the vagina, rectum or mouth, and even under the skin for subcutaneous administration. In an interesting use of my adhesive as a drug delivery medium, my adhesive is prepared so as to include an aqueous solution of epsom salt. A layer of the adhesive is applied to the feet, and the user is able to freely move about and still "soak" his feet. The adhesive will retain the epsom salt solution, and even if compressed will not release moisture. The pharmacologically active agent should be soluble in the plasticizer phase of the adhesive, and must be present in an amount sufficient to bring about the desired pharmacological effect. Exemplary pharmacologically active agents include hormones such as estrogen, analgesics, and antirheumatics. Additionally, the adhesive may be used as a carrier for a depilatory agent.

My adhesive is especially useful as a vibration or impact absorbing material such as a padding since it is very soft and can undergo considerable shear strain and yet not transmit very high stresses. A self-supporting layer of the adhesive may be used as padding in shoes, orthopedic devices, casts and splints. In another use as a padding, a layer of the adhesive may be used as a saddle blanket so as to reduce saddle sores of horses. My adhesive is useful for attenuating vibration in motion picture equipment, and in various sensitive instruments. Additionally, my adhesive provides good sound attenuation.

The properties of my adhesive result in usefulness for treating or preventing bed sores or decubitus ulcers. This is accomplished by applying a layer of my adhesive to a selected area of the body, as a result of which rubbing of this area is reduced.

My adhesive may contain beneficial ingredients such as humectants, skin conditioners, depilatories, hormones, perfumes, cleansing agents, acne medication, antiperspirants, astringents, sun screens, and artificial sun tanning materials. When used as medium for delivering an adhesive-soluble pharmacologically active agent, my adhesive may function to provide continuous drug delivery by providing an appropriate concentration of the drug in a suitable adhesive. In addition to those drug types set forth above, the drug could be nitroglycerin or a motion sickness treatment drug. In situations where it is desirable to have a bacteriastatic agent in the adhesive, for example, where the adhesive is to be applied to the face of a person for treatment of acne or is to be applied topically to the skin for treatment of a topical infection, my adhesive includes a quaternary ammonium compound. For treatment of ringworm, athlete's foot, jock itch or other topical fungal infections, an appropriate antifungal compound is added to my adhesive.

As a self-supporting layer, my adhesive may also be used to secure a prosthesis to a mammalian body. Also, an article of apparel may be secured to a mammalian body by use of a self-supporting layer of my adhesive.

In forming my adhesive, irradiation is used to induce cross-linking of an appropriate synthetic organic polymer. The use of an irradiation processing technique enables in situ preparation of films and coatings to be done continuously, and additionally enables bulk cross-linking, especially if gamma rays from cobalt 60 are used. Using irradiation to cross-link the synthetic organic polymer allows the use of high speed web processing techniques and thereby results in high volume continuous production of adhesive-coated substrate. Simple liquid handling equipment can be used to dispense the uncrosslinked formulation onto a moving web of substrate, which then passes under a scanning electron beam.

One potential problem of a polymer that has been chemically cross-linked may exist in the situation where an ester linkage has been formed by the reaction of a carboxyl group of the polymer with an oxirane or aziridine group of the cross-linker, and a significant amount of water is present. In this instance, the ester linkage may not be hydrolytically stable over a period of several weeks. Similarly, an amide bond formed between the carboxyl group of a polymer and the amine group of a cross-linking agent may not be hydrolytically stable. On the other hand, the carbon-carbon bonds formed between adjacent polymer molecules during irradiation are very stable. Further advantages of using irradiation are high efficiency, ease of handling, and the elimination of potentially toxic chemicals. Irradiation is a clean process that is thought to impart no residual chemical toxins. The advantages of easy handling and rapid processing equipment make the use of irradiation very cost effective. Cross-linking can be accomplished instantly rather than requiring prolonged cure cycles such as are required with an epoxy cure. A further advantage is that in certain instances when chemical cross-linking is used, the cross-linked polymeric material would have to be air dried to remove the water in order to convert the material from a flowable liquid state to a pressure-sensitive adhesive. In contrast, use of an appropriate dosage of irradiation would convert such a composition instantly to a pressure-sensitive adhesive.

A theoretical dose rate can be calculated for an electron beam by using the equation:

$$\frac{d}{t} = 1.1 \frac{I}{A},$$

assuming an energy loss similar to water, where d is the dose in megarads, t is the time in minutes, A is the area of the scanning electron beam in space meters, I is the current in milliamperes, and 1.1 is an empirical constant dependent upon the material being irradiated and a beam energy for 2 Mev. Using a scanning electron beam of 152.4 cm scanning width and a scanning length of 5.08 cm, and using current of 3–30 milliamperes, the theoretical dose rate is calculated to be $2.5-25 \times 10^9$ rads per hour. The material to be irradiated is passed under the scanning beam on a moving conveyor. In this instance, the conveyor travels in the direction of the 5.08 cm scanning coordinate so as to allow the conveyor to take advantage of the 152.4 cm width.

Using a 100 milliamp irradiation source, it may be possible to reach production rates as high as a million square feet per day. Since, in most embodiments, a volatile organic solvent is not used in making my adhesive, solvent removal to produce a "dry" adhesive does not necessitate expensive pollution control and explosion prevention equipment.

Under certain circumstances, a cross-linking promoter is advantageously added to the solution or dispersion of the uncrosslinked polymer. Exemplary promoters include polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercaptopropionate), trimethylolpropane trithioglycolate, dithioethane, di- or trithiopropane and 1,6-hexane dithiol.

In another emdobiment of my invention my adhesive is electroconductive and useful for attaching an electrically conductive member of an electrode to a selected surface such as mammalian tissue. Basically, this adhesive is the same adhesive as that discussed above except that a conductivity-enhancing material is included in the adhesive composition. Conveniently, the conductivity-enhancing material is added to the solution or dispersion of the uncrosslinked polymer prior to the irradiation treatment step. Preferably, the conductivity-enhancing material is a non-polymeric, ionizable organic or inorganic salt. The amount of the conductivity-enhancer to be used in my adhesive depends upon factors such as the conductivity-enhancing material selected, with a relatively smaller amount of a more conductive material being required, and a relatively greater amount of a material providing relatively less conductivity, being needed. Exemplary non-polymeric, ionizable organic or inorganic salts include ammonium sulfamate, monoethanolamine acetate, diethanolamine acetate, sodium lactate, sodium citrate, sodium chloride, magnesium sulfate, and polyethylene glycol-soluble salts such as ammonium acetate, magnesium chloride and magnesium acetate. About 5% of magnesium sulfate, about 5-7% of magnesium acetate or about 7% of ammonium acetate is suitably used as the conductivity-enhancer in my adhesive. Mixtures of conductivity-enhancing materials may be used. Thus, for example, a mixture of magnesium chloride and magnesium acetate could be utilized.

My electroconductive adhesive is particularly suitable for use as an electrode adhesive, and thus is conveniently used as a coating on an electrically conductive substrate such as member 12 of FIG. 1. Electrically conductive members are well known in the electrode art. Thus, a discussion is not provided concerning such a member except to point out that the selection of the particular material to be used to form the member, as well as selection of the size, shape and thickness, is dependent on the end use contemplated for the electrode. Generally, member 12 has a thickness ranging from about 15 thousandths up to about ⅛ inch. As shown in FIG. 1, electroconductive adhesive 14 serves to attach member 12 to a surface 16. The electroconductivity of the adhesive promotes the transfer of electric signals between member 12 and surface 16. Exemplary electrodes for attachment to mammalian skin include a transcutaneous electrical nerve stimulation electrode, an electrosurgical return electrode and an EKG monitoring electrode.

Examples of my invention will now be provided in order to illustrate the invention. These examples are to be regarded as exemplary only. All percentages are weight percent unless otherwise indicated.

EXAMPLE 1

A solution coontaining 20% PVP, 25% PEG and 55% water was prepared, and a 1.5 mm coating of the solution was applied to one side of a white polyester cloth. The PVP was PVP K-90 sold by GAF, the PEG was Carbowax ®300 sold by Union Carbide, and the cloth is similar to the fabric customarily making up a nurse's uniform. A protective polyethylene film was applied to the coated fabric, and the sample was subjected to an ionizing irradiation dose of 3.5 megarads using a 2.5 Mev electron beam source. This procedure was repeated several times to produce a number of samples. The polyethylene film was removed from approximately half of the samples, and these particular samples were allowed to air dry for about 48 hours at approximately 30% relative humidity and 20° C., to form "dry" samples. The "wet" and "dry" samples were then subjected to a rolling ball tack test, and tested for peel strength and lap shear. The rolling ball tack test was conducted as follows: A steel ball was rolled down an inclined trough of 8.3" length and having a cross-sectional width of 0.53 inches (the trough being inclined at an angle of 21 degrees 30 minutes from the horizontal). The adhesive sample was positioned so that as the ball rolled off the end of the trough, the ball began contacting the surface of the adhesive sample. A relatively lower number means the adhesive had a better tack.

The samples were tested for 180° peel as follows: A 4" length of a specimen of 1" width was caused to adhere to one surface of a vertically-oriented steel plate, the remaining length of the specimen was doubled back, and the loose end of the remaining length was anchored. The steel plate was pulled vertically upward at a speed of 6" per minute, and the force to strip the adhesive sample from the vertically oriented steel plate surface was measured.

Each sample was analyzed for 90° peel as follows: A 6" length of a specimen of 1" width was caused to adhere to one surface of a vertically-oriented steel plate and the remaining 6" length of the specimen was caused to adhere to the top surface of a horizontally oriented steel plate. The vertically oriented steel plate was moved vertically upward at a speed of 6" per minute, and the force to strip the adhesive sample from the horizontal plate surface was measured. The specimens for the peel strength testing showed a wide variance in thickness within a given specimen type. Also, the specimens contained air bubbles.

In addition, the solution of PVP, PEG, and water was used to saturate a piece of gauze with about 1 mm of adhesive, and the saturated gauze was placed between two polyethylene sheets, and irradiated in like manner as before. This procedure was repeated to produce additional samples for testing for water vapor transmission and oxygen permeance. Prior to this testing, the upper layer of polyethylene was removed in the case of about half the samples, and these particular samples were allowed to air dry for about 48 hours at approximately 30% relative humidity and 20° C. to produce "dry" samples.

Oxygen permeance was measured as follows: An adhesive sample having an area of 3.4 in$^2$ and a thickness of 0.15 inches was located between two chambers, with one side of the adhesive sample forming a portion of one chamber wall, and the other side of the sample forming a portion of the other chamber wall. Oxygen was flowed from a regulator through a gas flow meter into a reservoir connected to a manometer. A 1 psi $O_2$ pressure difference was set up between the two chambers, and the oxygen permeance is measured.

The results for the rolling ball tack test, peel strength test, lap shear test, and oxygen permeance are shown in Table 1. The water vapor transmission results are set forth in Table 2.

EXAMPLES 2-44

Adhesives in accordance with the invention, certain of which are conductive, were prepared using the formulations shown in Table 3. In each case, a solution or dispersion was formed, and a layer ranging from about 1-6 mm in thickness was subjected to a dose of a 2.5 Mev electron beam radiation source, as indicated in the Table. The layer thickness ranged from about 1-3 mm for formulations containing PVP and PEG, and ranges from about 2-6 mm for the other formulations, In each instance, the resulting cross-linked material was adhesive.

In addition, several of the cross-linked adhesives were allowed to air dry for about 48 hours at approximately 30% relative humidity and 20° C. For these particular formulations, the theoretical formula of the corresponding dry adhesive is shown in the Table. In all cases, the corresponding "dry" material was a good adhesive.

COMPARATIVE EXAMPLES 1-5

Following the procedure of Examples 2-44, a solution or dispersion of each of the formulations shown in Table 4 was prepared, and a layer ranging in thickness from about 2-6 mm was subjected to a dose of 2.5 Mev electron beam radiation, as indicated in this Table. In each case, the resulting cross-linked material was adhesive. Each of these adhesives was allowed to air dry in the same manner as each of the adhesives of Examples 2–44 for which a theoretical formula of the corresponding "dry" adhesive is shown. "Dry" comparative material 1 was a non-adhesive brittle film, and the other four "dry" comparative materials were non-adhesive flexible films.

EXAMPLE 45

A conductive adhesive was prepared using the following formulation:

| | |
|---|---|
| Polyvinyl pyrrolidone (PVP K-90, GAF) | 20% |
| Polyethylene glycol 300 (Carbowax 300 Sentry Grade, Union Carbide) | 25% |
| Magnesium Acetate (Reagent Grade, J. T. Baker) | 7% |
| Methyl paraben (Inolex) | .037% |
| Propyl Paraben (Inolex) | .012% |
| FD & C Blue #2 (H. Kohnstamm) | .0012% |
| Water | Balance |

A 1/15 inch thick layer of the viscous liquid was applied to the electrosurgical return electrode pad of FIG. 1. This pad had 20 square inches of electrode area. The coated pad was then subjected to 3.5 megarads of 2.5 Mev electron beam radiation.

The electrical impedance of the electrode was measured by constructing a circuit in which an electrical current was passed through the entire area of the electrode. This was done by first securing the full surface of the electrode to a stainless steel plate. The stainless steel plate was then connected to the active electrode of a Valleylab SSE3-B electrosurgical generator, while the electrode being tested was grounded to the generator ground. A Simpson radiofrequency ammeter was connected in series with the electrode/stainless plate and a Fluke model 8920A true RMS voltmeter was connected between the steel plate and the electrode. The SSE3-B generator was adjusted to produce a 750,000 hertz sine wave signal, and the current was adjusted to one amp using the Simpson ammeter as a reference. The voltage was read on the voltmeter and recorded. The result is shown in Table 5, as average impedance per square inch.

The peel strength at 180° was tested using a steel plate, as in the Table 1 peel strength data, and was also tested using the skin of female and male human test subjects. The procedure used was essentially the same as that set forth with respect to the 180° peel test of Table 1, except that the tensile tester was used to peel off the electrode at a rate of 12 inches per second. Furthermore, in carrying out the test with human test subjects, the electrode pad was pulled off manually using a hand-held Ametek 0–30 pound scale. In each of these experiments, the electrode pad was secured to the thigh of the test subject. Attention was invited to Table 6, which shows the results.

The adhesive of the electrode pad was tested for any irritating effect upon human subjects, with particular attention being given to discomfort upon removal, pulling of hair, edema, erythema, bruising and removal of epidermis. The electrode pad was applied to the subject and removed within ten minutes, with the runs being uniformly carried out. The data obtained is set forth in Table 7.

Electrical impedance of the electrode was tested on human test subjects using one amp of current at 750,000 hertz. The runs were uniformly conducted, and the data obtained is shown in Table 5, as average impedance per square inch.

Further testing of the electrode pad was carried out by weighing the pad and heat sealing it into an alumimum foil laminate pouch having a moisture vapor transmission rate not greater than 0.016 g/100 in$^2$/24 hrs. when tested at 37° C. with 90% relative humidity on one side and dry air on the other. This procedure was repeated several times, and the sealed pads are placed into a Blue M oven at the same time. At two week intervals, six of the pouches were removed and allowed to stand at room temperature for 18 hours. The pouches were then opened, the pads removed, the pads reweighed, and then electrical impedance and adhesion to a metal plate were tested. The results of this testing are set forth in Table 8.

Petri dish samples of the irradiated adhesive were prepared and tested to see whether the irradiated adhesive supports bacterial or mold growth. Each of four plates was inoculated with *Serratia marcescens, Micrococcus lutea, E. coli* and *Candida albicans*. One of these inoculated plates was incubated for two weeks at 2° C., another at 25°·C., a third at 37° C. and the fourth at 55° C. A fifth plate was left sealed at room temperature as a negative control. A sixth plate was left open for 15 minutes to room air in a biology lab and allowed to incubate at 25° C. for one week and 37° C. for an additional week. None of the six plates showed any colony growth. As a positive control, an agar plate containing minimum nutrients was inoculated with the same bacterial and yeast and incubated at 37° C. Colony growth is seen on this plate after 24 hours.

COMPARATIVE EXAMPLE 6

A commercially available electrosurgical pad is used for comparison with the electrode pad of Example 45. This pad, which was designated "Comparative Pad" throughout this specification, had a viscous gel impregnated in a reticulated polyurethane sponge, and had a conventional pressure-sensitive adhesive along the border for adhering the pad to a surface such as mammalian skin. The electroconductive member of the pad was a nickel alloy, and the viscous gel was comprised of 3% Carbopol ®934, 3% sodium sodium chloride, sufficient sodium hydroxide to adjust the pH to 7.0, and water.

The various testing carried out on the electrode pad of Example 45 was repeated in the same manner, except that inoculation with bacteria and yeast was not carried out. Additionally, the testing involving use of the Blue M oven was conducted so that these samples and the other samples were placed into the oven at the same time and also removed from the oven and otherwise treated at the same time. In Tables 5–8, the data obtained are set forth.

EXAMPLE 46

A conductive adhesive was prepared using the procedures of Example 45 having the following formulation:

| Ingredient | Percent by Weight |
|---|---|
| Polyvinylpyrrolidone (PVP K 90, GAF) | 20 |
| Polyethylene glycol 300 (Carbowax 300 Sentry Grade, Union Carbide) | 25 |
| Magnesium Acetate (Reagent Grade, J.T. Baker) | 5 |
| Water | 50 |

| Ingredient | Percent by Weight |
|---|---|
| Ultramarine Blue (Whitaker, Clark & Daniel | 0.5 |

Industrial Applicability

The present invention is concerned with a novel water-insoluble, hydrophilic, elastomeric, pressure-sensitive adhesive. This adhesive is useful either as a coating on a supportive web-like substrate or as a self-supporting layer. When supported by a web-like substrate, this adhesive is useful as an adhesive on a bandage, a wound or burn dressing, a sanitary napkin, a diaper, an ostomy device, a decubitus ulcer pad, a vibration or impact absorbing material, a sound absorbing material, and a medium for delivering a pharmacologically active agent (drug). In addition, when used as a self-supporting layer, this adhesive is useful as a cosmetic face mask and for securing a prosthesis or article of apparel to a mammalian body. In one embodiment of the adhesive, the adhesive is electrically conductive and is useful as an electrode adhesive. Illustrative electrodes include a transcutaneous electrical nerve stimulation electrode, an electrosurgical return electrode, and an EKG monitoring electrode.

TABLE 1

|  | Average | Standard Deviation |
|---|---|---|
| Rolling Ball Tack Test (ASTM D3121) | | |
| (A) Dry (5 runs) | 0.04" | 0.005 |
| (B) Wet (5 runs) | 0.03" | 0.002 |
| Peel Strength 180° Peel (ASTM 903) | | |
| (A) Dry (2 runs) | 2.57 lb/in width | 0.69 |
| (B) Wet (3 runs) | 0.43 lb/in width | 0.09 |
| Peel Strength 90° Peel (ASTM D1876) | | |
| (A) Dry (4 runs) | 4.34 lb/in width | 1.82 |
| (B) Wet (3 runs) | 0.98 lb/in width | 0.19 |
| Lap Shear | | |
| (A) Dry (2 runs) | 1.98 psi | 0.46 |
| (B) Wet (2 runs) | 0.054 psi | 0.05 |
| Oxygen Permeance (standard cubic feet $O_2$/hour/inch$^2$ at 1 psi pressure drop) | | |
| (A) Dry | 5.1 | — |
| (B) Wet | — | — |

TABLE 2

Water Vapor Transmission (ASTM 3833)[1]

|  | Wet | | Dry | |
|---|---|---|---|---|
|  | A1 | A2 | B1 | B2 |
| Initial Weight $CaCl_2$ (g) | 22.36 | 13.80 | 23.97 | 20.39 |
| Initial Weight Sample (g) | 12.04 | 14.70 | 7.73 | 6.40 |
| $H_2O$ Absorbed $CaCl_2$ (g) | 12.32 | 11.02 | 14.30 | 15.40 |
| $H_2O$ Absorbed as a percent of initial sample weight | 11.89 | 4.63 | 28.98 | 29.84 |
| Actual Weight Gain Sample (g) | 1.43 | 0.68 | 2.24 | 1.91 |
| Water Vapor Transmission Rate g/100 in$^2$ | 353.94 | 316.67 | 410.92 | 442.43 |
| Thickness[2] (inches) | 0.12 | 0.10 | 0.07 | 0.06 |
| Std. Dev. | 0.03 | 0.04 | 0.01 | 0.01 |

[1]The conditions maintained in the sealed chamber were 90–95% humidity and 100° F. ± 1°. The samples were conditioned for 24 hours. Since the dessicant, $CaCl_2$, reached 100% absorbency in 24 hours, the test was concluded.
[2]Each value represents an average of 5 readings across each sample.

TABLE 3[1]

| Example | Polymer (%) | Plasticizer (%) | Dose (MR) | Theoretical Formula of Dry Adhesive |
|---|---|---|---|---|
| 2 | PVA (18%) | PEG 300 (10%) Water (72%) | 2 | |
| 3 | PVP (22.5%) | PEG 300 (10%) Water (67.5%) | 1.5 | |
| 4 | PVP (20%) | PEG 300 (20%) Water (60%) | 2 | |
| 5 | PVP (17.5%) | PEG 300 (30%) Water (52.5%) | 2 | |
| 6 | PVP (15%) | PEG 300 (40%) Water (45%) | 2 | |
| 7 | PVP (12.5%) | PEG 300 (50%) Water (37.5%) | 2 | |
| 8 | PVP (18%) | PEG 300 (10%) Water (72%) | 2 | |
| 9 | PVP (16%) | PEG 300 (20%) Water (64%) | 2 | |
| 10 | PVP (14%) | PEG 300 (30%) Water (56%) | 2 | 32% PVP 68% PEG 300 |
| 11 | PVP (20%) | PEG 300 (10%) Water (70%) | 3.5 | 67% PVP 33% PEG 300 |
| 12 | PVP (20%) | PEG 300 (15%) Water (65%) | 3.5 | 57% PVP 43% PEG 300 |
| 13 | PVP (20%) | PEG 300 (20%) Water (60%) | 3.5 | 50% PVP 50% PEG 300 |
| 14 | PVP (20%) | PEG 300 (25%) Water (55%) | 3.5 | 45% PVP 55% PEG 300 |
| 15 | PVP (20%) | PEG 300 (30%) Water (50%) | 3.5 | 40% PVP 60% PEG 300 |

TABLE 31-continued

| Example | Polymer (%) | Plasticizer (%) | Dose (MR) | Theoretical Formula of Dry Adhesive |
|---|---|---|---|---|
| 16 | PVP (20%) | PEG 300 (35%) Water (45%) | 3.5 | 36% PVP 64% PEG 300 |
| 17 | PVP (20%) | PEG 300 (40%) Water (40%) | 3.5 | 33% PVP 67% PEG 300 |
| 18 | PVP (20%) | PEG 300 (50%) Water (30%) | 3.5 | 29% PVP 71% PEG 300 |
| 19 | PVP (20%) | PEG 300 (60%) Water (20%) | 3.5 | 25% PVP 75% PEG 300 |
| 20 | PVP (20%) | PEG 300 (70%) Water (10%) | 3.5 | 22% PVP 78% PEG 300 |
| 21[2] | PVP (20%) | PEG 300 (30%) Water (43%) | 3.5 | 35% PVP 53% PEG 300 |
| 22[3] | PVP (20%) | PEG 300 (10%) Water (65%) | 2 |  |
| 23 | PVP (7.5%) 20% Gafquat® 755 N in H$_2$O (62.5%) | PEG 300 (30%) | 3.5 | 15% PVP 25% Gafquat® 60% PEG 300 |
| 24 | PVP (15.8%) 20% Gafquat® 755 N in H$_2$O (20.8%) | PEG 600 (30%) Water (33.3%) | 2.5 | 31.4% PVP 8.6% Gafquat® 60% PEG 600 |
| 25 | PVP (11.6%) 20% Gafquat® 755 N in H$_2$O (41.7%) | PEG 600 (30%) Water (16.7%) | 4 | 23.2% PVP 16.8% Gafquat® 60% PEG 600 |
| 26 | PVP (2.5%) 20% Gafquat® 755 N in H$_2$O (87.5%) | PEG 600 (10%) | 2.5 | 8.3% PVP 58.3% Gafquat® 33.3% PEG 600 |
| 27 | PVP (5.0%) 20% Gafquat® 755 N in H$_2$O (75%) | PEG 600 (20%) | 3 | 12.5% PVP 37.5% Gafquat® 50% PEG 600 |
| 28 | PVP (15.8%) 20% Gafquat® 755 N in H$_2$O (20.8%) | PEG 300 (30%) Water (33.3%) | 3 | 31.4% PVP 8.6% Gafquat® 60% PEG 300 |
| 29 | PVP (11.6%) 20% Gafquat® 755 N in H$_2$O (41.7%) | PEG 300 (30%) Water (16.7%) | 2.5 | 23.2% PVP 16.8% Gafquat® 60% PEG 300 |
| 30 | PVP (5%) 20% Gafquat® 755 N in H$_2$O (75%) | PEG 300 (20%) | 3.5 | 12.5% PVP 37.5% Gafquat® 50% PEG 300 |
| 31 | 20% Gafquat® 755 N in H$_2$O (90%) | PEG 300 (10%) | 3.5 | 64% Gafquat® 36% PEG 300 |
| 32[4] | PAA (20%) | PEG 300 (20%) Water (52%) | 3 |  |
| 33[5] | PAA (17.5%) | PEG 300 (30%) Water (45.5%) | 3.5 |  |
| 34[6] | PAA (20%) | PEG 600 (10%) Water (62%) | 2.5 |  |
| 35[7] | PAA (20%) | PEG 600 (20%) Water (52%) | 2.5 |  |
| 36[8] | PAA (17.5%) | PEG 600 (30%) Water (45.5%) | 3 |  |
| 37 | PAA (15%) | PEG 300 (42.5%) Water (42.5%) | 3 | 26% PAA 74% PEG 300 |
| 38 | PAA (15%) | PEG 300 (34%) Water (51%) | 1.5 | 31% PAA 69% PEG 300 |
| 39 | PAA (15%) | PEG 300 (25.5%) Water (59.5%) | 1.5 | 40% PAA 60% PEG 300 |
| 40 | PAA (14%) Polyethylene oxide[9] (1%) | PEG 300 (20%) Water (65%) | 2.5 |  |
| 41 | PAA (18.8%) | PEG 600 (20%) Water (61.2%) | 2 | 49% PAA 51% PEG 600 |
| 42 | PVP (20%) | Sorbitol (30%) Water (50%) | 3.5 |  |
| 43 | PVP (20%) | Sorbitol (15%) Water (65%) | 3.5 |  |
| 44 | MVE/MA (20%) | PEG 600 (20%) | 3.5 | 50% MVE/MA |

TABLE 3-continued

| Example | Polymer (%) | Plasticizer (%) | Dose (MR) | Theoretical Formula of Dry Adhesive |
|---|---|---|---|---|
| | | Water (60%) | | 50% PEG 600 |

TABLE 3 - Footnotes
[1] PVA is polyvinyl alcohol.
PAA is polyacrylic acid having a molecular weight of approximately 450,000 and sold by B. F. Goodrich as Carbopol ® 907.
MVE/MA is GAF's brand of copolymer of methyl vinyl ether and maleic anhydride.
The PVP is PVP K-90.
[2] The "wet" formula additionally contained 7% ammonium acetate. This was a conductive adhesive.
[3] This formula additionally contained 5% magnesium sulfate. This was a conductive adhesive.
[4] This formula additionally contained 8% of 30% ammonium hydroxide solution.
[5] This formula additionally contained 7% of 30% ammonium hydroxide solution.
[6] This formula additionally contained 8% of 30% ammonium hydroxide solution.
[7] This formula additionally contained 8% of 30% ammonium hydroxide solution.
[8] This formula additionally contained 7% of 30% ammonium hydroxide solution.
[9] This is a 4 million molecular weight polymer sold by Union Carbide under the trademark Polyox WSR-Coag.

TABLE 4*

| Comparative Example | Polymer (%) | Plasticizer (%) | Dose (MR) | Theoretical Formula of Dry Adhesive |
|---|---|---|---|---|
| 1 | PVP (20%) | Water (80%) | 3.5 | 100% PVP |
| 2 | PVP (19.8%) | PEG 300 (1.0%) Water (79.2%) | 1.5 | 95% PVP 5% PEG 300 |
| 3 | PVP (19.6%) | PEG 300 (2.2%) Water (78.2%) | 1.5 | 90% PVP 10% PEG 300 |
| 4 | PVP (19.3%) | PEG 300 (3.4%) Water (77.3%) | 1.5 | 85% PVP 15% PEG 300 |
| 5 | PVP (19.0%) | PEG 300 (4.8%) Water (76.2%) | 1.5 | 80% PVP 20% PEG 300 |

*The PVP is PVP K-90.

TABLE 5

(Impedance Test)

| | Average Impedance per square inch[1] (ohms/sq. in.) | Standard Deviation Per sq. in. (ohms/sq. in.) | Ratio of Std. Deviation per sq. in. to Avg. Impedance per sq. in. (Measure of Product Uniformity) |
|---|---|---|---|
| Using Stainless Steel Plate | | | |
| (A) Example 45 Pad[2] | 0.070 | 0.020 | — |
| (B) Comparative Pad[3] | 0.078 | 0.018 | — |
| Using Human Subjects | | | |
| I. Male | | | |
| A. Example 45 Pad[2] | 0.586 | 0.163 | 0.279 |
| B. Comparison Pad[3] | 0.387 | 0.108 | 0.323 |
| II. Female | | | |
| A. Example 45 Pad[2] | 0.878 | 0.267 | 0.304 |
| B. Comparison Pad[3] | 0.574 | 0.185 | 0.322 |

[1] Each value represents 15 runs.
[2] This pad had an active electrode area of 20 square inches.
[3] This pad had an active electrode area of 24 square inches.

TABLE 6

(Peel Strength - 180°)[1]

| | Average Adhesion (lbs/in. width) | Standard Deviation (lbs/in. width) | Ratio of Standard Deviation to Average Adhesion (Measure of Product Uniformity) |
|---|---|---|---|
| I. Using Steel Plate | | | |
| A. Example 45 Pad | 0.362[2] | 0.043 | 0.121 |
| B. Comparative | 0.945[2] | 0.196 | 0.207 |
| II. Using Thigh of Female Human Subjects | | | |
| A. Example 45 Pad | 0.42[3] | 0.043 | 0.24 |
| B. Comparative Pad | 0.79[3] | 0.31 | 0.39 |
| III. Using Thigh of Male Human Subjects | | | |
| A. Example 45 Pad | 0.43[3] | 0.09 | 0.21 |
| B. Comparative Pad[4] | — | — | — |

[1] In carrying out these tests, it was noted that the pull force remains relatively more constant with the Example 45 pad than the comparative pad.
[2] This value represents 30 runs.
[3] This value represents 15 runs.
[4] Data were not taken since the male subjects, with their unshaven legs, experience painful pulling upon pad removal.

TABLE 7

| % of Human Subjects Experiencing Irritation Upon Pad Removal* | |
|---|---|
| I. Male | |
| (A) Example 45 Pad | 0 |
| (B) Comparative Pad | 47 |
| II. Female | |
| (A) Example 45 Pad | .06 |
| (B) Comparative Pad | 66 |

*Fifteen tests were carried out for each pad type.

TABLE 8[1]

| Impedance Test Using Stainless Steel Plate[2] | Average Impedance (ohms) | | | Standard Deviation (ohms) | | |
|---|---|---|---|---|---|---|
| | week 2 | week 4 | week 6 | week 2 | week 4 | week 6 |
| (A) Heat-Aged Example 45 Pad | 1.261 | 1.208 | 1.372 | 0.306 | 0.373 | 0.226 |
| (B) Heat-Aged Comparative Pad | 0.710 | 0.810 | 1.116 | 0.129 | 0.080 | 0.166 |
| Peel Strength - 180° Using Stainless Steel Plate[4] | Average Adhesion (g/in. width)[3] | | | Standard Deviation (g/in. width) | | |
| (A) Heat-Aged Example 45 Pad | 142.7 | 139.2 | 142.1 | 10.8 | 37.1 | 38.4 |
| (B) Heat-Aged Comparative Pad | 555.4 | 435.8 | 487.5 | 211.8 | 69.7 | 37.9 |
| | Average Weight Loss (%)[5] | | | Standard Deviation | | |
| (A) Heat-Aged Example 45 Pad | −0.5 | N/A | −0.8 | 0.2% | N/A | 0.7% |
| (B) Heat-Aged Comparative Pad | −0.8 | N/A | −3.9 | 0.5% | N/A | 2.8% |

[1] The samples were aged at 55° C. in a Blue M oven, Model E20043-1.
[2] The impedance test on these aged samples was run identically to the Table 5 impedance test using a stainless steel plate.
[3] Each value represents 6 runs.
[4] The peel strength test on these aged samples was run identically to the Table 6 peel strength test using a stainless steel plate.
[5] Each value represents 36 runs.

I claim:

1. An electroconductive, water-insoluble, hydrophilic, elastomeric pressure-sensitive adhesive comprising a gel of polyvinylpyrrolidone cross-linked by ionizing radiation, a polyalkylene glycol plasticizer, water and a salt selected from ammonium acetate, magnesium acetate or magnesium sulfate, wherein said cross-linked gel is formed by irradiation of a solution or dispersion of said salt and said polyvinylpyrrolidone in said water and said plasticizer; and wherein said cross-linked gel retains said plasticizer within a cross-linked three-dimensional matrix of said polyvinyl pyrrolidone.

2. The adhesive of claim 1 wherein said plasticizer is present in an amount ranging from about 0.5 to 4 times the weight of said polymer.

3. The adhesive of claim 1 wherein said salt is magnesium acetate.

4. The adhesive of claim 1 wherein said plasticizer is polyethylene glycol.

5. The adhesive of claim 4 wherein said glycol has a molecular weight of about 300 or 600.

6. The adhesive of claim 5 wherein said glycol is present in an amount that is from about 0.75 to 1.5 times the weight of said pyrrolidone.

7. The adhesive of claim 1 wherein the said solution or dispersion comprises
   (a) about 18 to 22 percent by weight of polyvinyl pyrrolidone,
   (b) about 25 percent by weight of polyethylene glycol having a molecular weight of about 300,
   (c) about 5 to 7 percent by weight of magnesium acetate, and
   (d) water.

8. An electrode comprising an electrically conductive member and the electroconductive adhesive of claim 1, said adhesive being adapted to attach said member to mammalian skin.

9. The electrode of claim 8 which comprises an electrosurgical return electrode, a transcutaneous electrical nerve stimulation electrode or an EKG monitoring electrode.

10. The electrode of claim 8 which comprises an electrosurgical return electrode.

11. The electrode of claim 8 wherein said electroconductive adhesive is coated on a web-like substrate.

12. An electrosurgical return electrode comprising an electrically conductive member in electroconducting association with an electroconductive pressure-sensitive adhesive coated on a web-like substrate and adapted to attach said member to mammalian skin,
   said adhesive being a radiation cross-linked gel comprising
   about 20 percent by weight of K-90 polyvinyl pyrrolidone,
   about 25 percent by weight of polyethylene glycol having a molecular weight of about 300,
   about 5 percent by weight of magnesium acetate, and
   about 50 percent by weight of water.

13. The electrode of claim 12 wherein said adhesive contains a compatible preservative.

* * * * *